(12) United States Patent
Banks

(10) Patent No.: US 7,595,032 B2
(45) Date of Patent: Sep. 29, 2009

(54) PROTECTED SEAL FOR A FILTERED VENT IN A STERILIZATION CONTAINER

(76) Inventor: Percival C. Banks, 1301 Quarry Ct., Suite 204, Point Richmond, CA (US) 94801

( * ) Notice: Subject to any disclaimer, the term of this patent is extended or adjusted under 35 U.S.C. 154(b) by 610 days.

(21) Appl. No.: 10/796,643

(22) Filed: Mar. 8, 2004

(65) Prior Publication Data
US 2005/0194387 A1 Sep. 8, 2005

(51) Int. Cl.
*A61L 2/00* (2006.01)
*A61L 9/00* (2006.01)
*B65D 51/16* (2006.01)

(52) U.S. Cl. .................. 422/292; 220/371; 220/372

(58) Field of Classification Search .......... 422/292, 422/310; 119/417; 30/411; 40/724; 47/66.2; 220/371, 372
See application file for complete search history.

(56) References Cited

U.S. PATENT DOCUMENTS 3,432,177 A * 3/1969 Colwell .................. 277/595
4,512,498 A * 4/1985 Leibinger ................ 220/371
4,551,311 A * 11/1985 Lorenz .................... 422/300
4,562,047 A * 12/1985 Sestak et al. ............. 422/300
4,661,326 A * 4/1987 Schainholz ............... 422/310
4,671,943 A * 6/1987 Wahlquist ................ 422/300
4,783,321 A * 11/1988 Spence .................... 422/300
4,915,913 A * 4/1990 Williams et al. .......... 422/119
4,948,566 A * 8/1990 Gabele et al. ............ 422/107
4,971,774 A * 11/1990 Schwanke et al. ........ 422/310
5,361,928 A * 11/1994 Stolzman ................. 220/378
5,968,459 A * 10/1999 Nalepa et al. ............ 422/300
6,041,741 A * 3/2000 Gabriel et al. ........... 119/417
6,620,390 B1 * 9/2003 Wagner ................... 422/297

FOREIGN PATENT DOCUMENTS

WO  WO 99/27969  *  6/1999
WO  WO 99/40948  *  8/1999

* cited by examiner

*Primary Examiner*—Elizabeth L McKane
*Assistant Examiner*—Regina Yoo
(74) *Attorney, Agent, or Firm*—H. Michael Brucker

(57) ABSTRACT

A sterilization container having a recess that surrounds a vent and a gasket in the recess and a filter cover that has a ridge matching the recess such that when the cover is locked in place, the cover ridge fits into the container recess and applies pressure against the gasket.

4 Claims, 4 Drawing Sheets

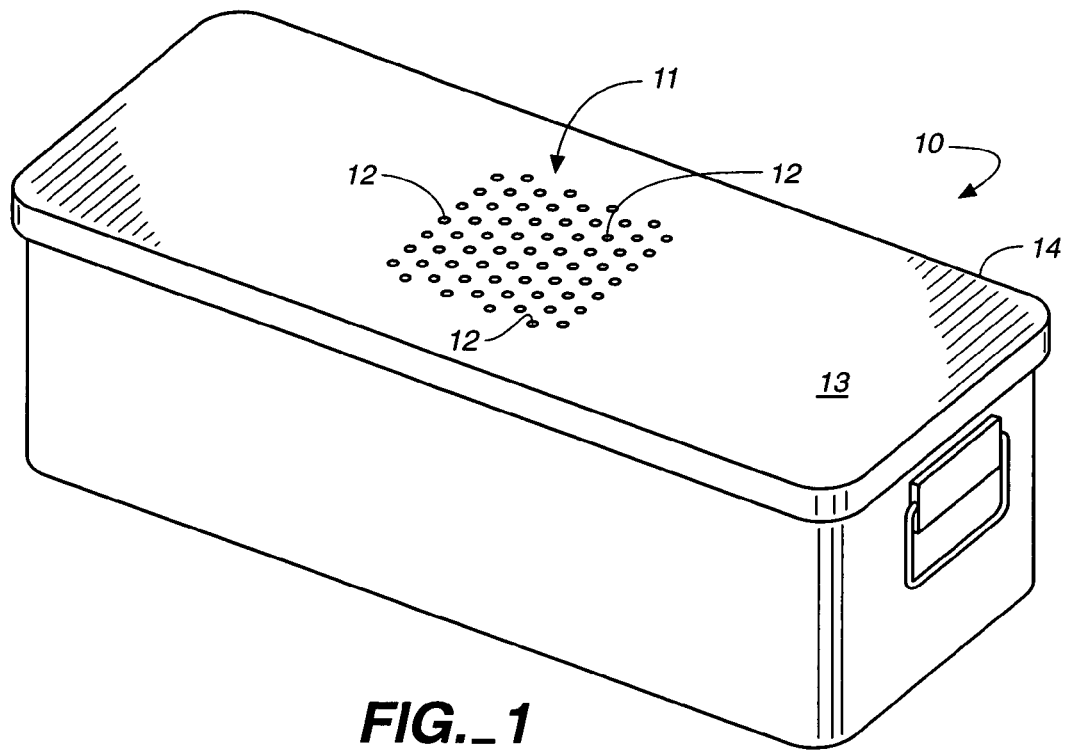
FIG._1
*(PRIOR ART)*
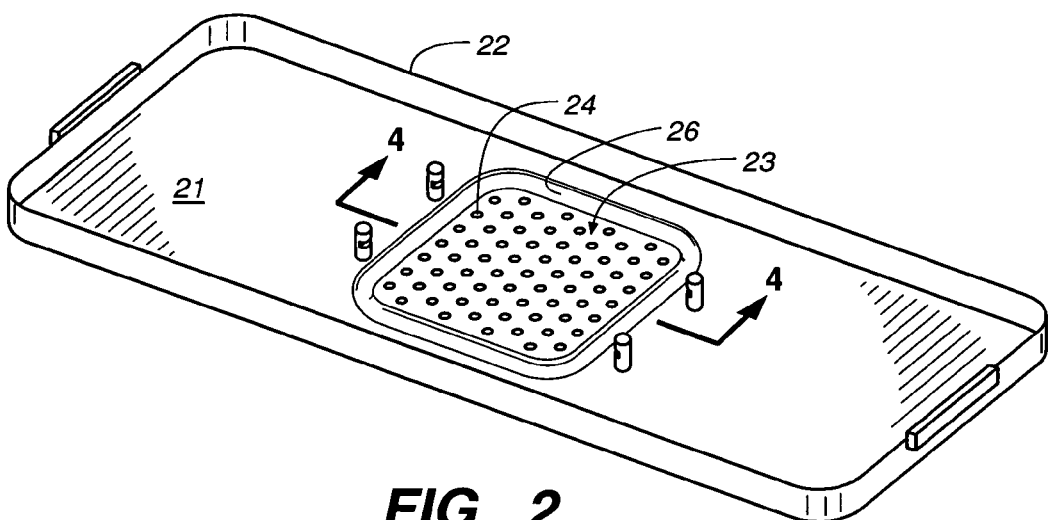
FIG._2

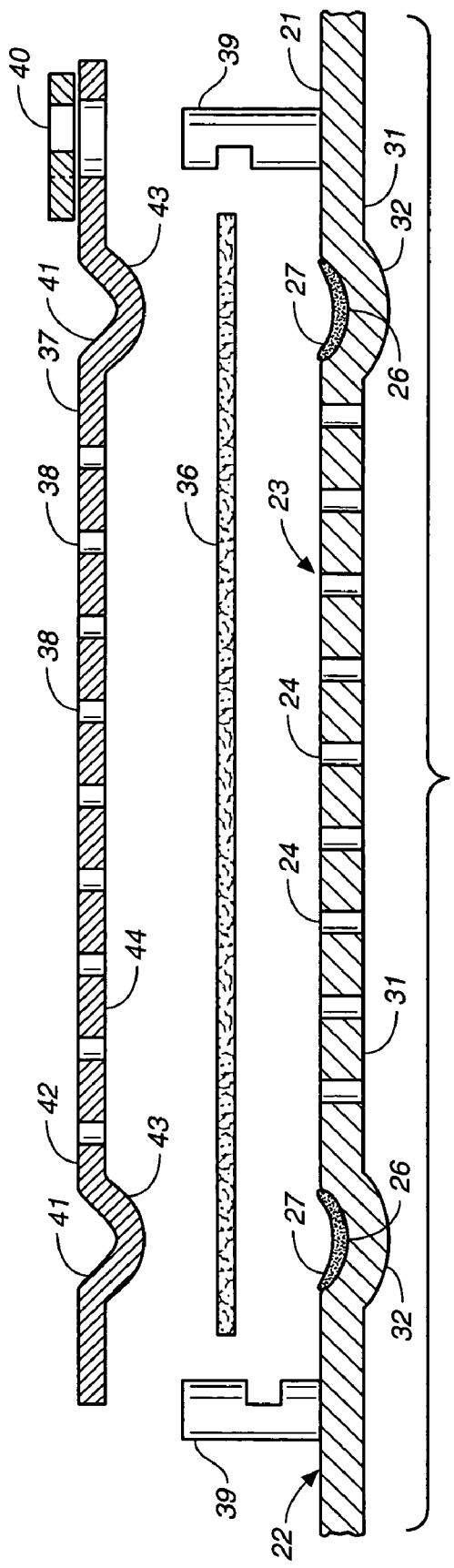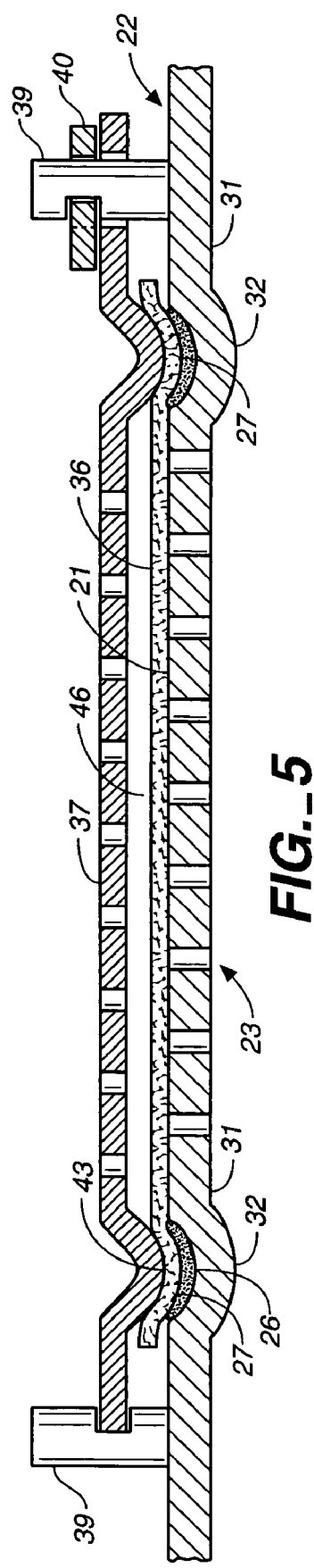

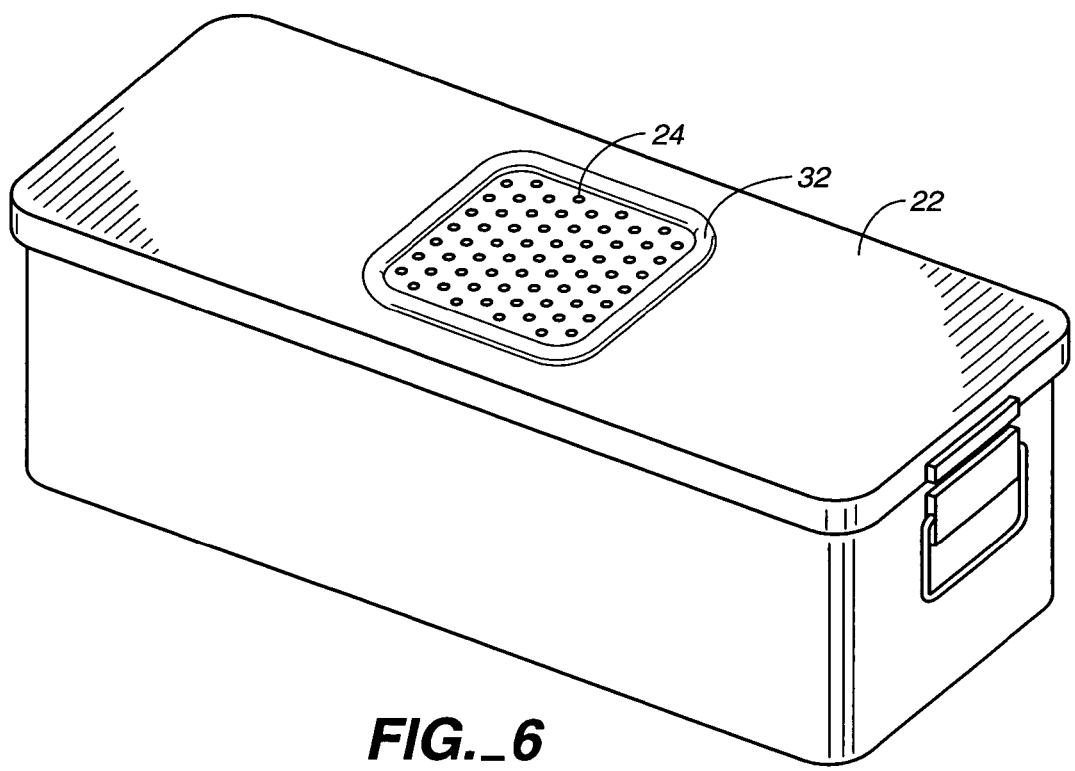
FIG._6

US 7,595,032 B2

PROTECTED SEAL FOR A FILTERED VENT IN A STERILIZATION CONTAINER

BACKGROUND OF THE INVENTION

Acute care facilities rely on rigid containers for the sterilization, handling and storage of surgical instrumentation and supplies. It is imperative that after sterilization, the sterile surgical instruments and supplies not be exposed to contaminates while still in the sterilization container.

Rigid sterilization containers commonly have a filtered vent (or vents) in the lid or other part of the container consisting of a patterned group of small holes. The floor of the container may also have a vent (or vents) which usually mirrors the number, size and placement of the vent or vents in the lid. See, for example, my U.S. Pat. No. 6,319,481 B1. Typically, each vent will have a sheet filter that covers the vented area and is held in place by a locking filter cover.

One commercially available sheet filter suitable for use with the present invention and with sterilization protocols is a 1.4 osy (ounces per square yard) basis weight Securon SMS manufactured by BBA Non-Wovens. Other suitable sheet filters are also commercially available. These special filter materials are characterized by the property that they are porous at elevated temperatures to allow sterilization media to pass and non-porous at lower temperatures.

Thus, the vent, with the filter element held in place by a filter cover, allows for the entry of the sterilizing media and exit of the displaced atmosphere during the sterilization cycle. Following sterilization, the filter provides a bacterial barrier to protect the sterile integrity of the contents during storage and transport.

As the sterilizing media is introduced into the sealed container, condensation can form and collect inside the container. Retained moisture in the form of condensation may be a by-product of either steam autoclaving or alternative low temperature sterilization methods.

In addition to steam autoclaving, "flash" processing is a commonly used method of rapid steam sterilization. Since "flash" steam sterilization protocols have either a limited or no drying cycle, retained moisture is a persistent condition. Since bacteria have no form of self-propulsion or locomotion, they need fluid pathways or small particles as a vehicle or conduit for their movement and/or dispersal.

Whenever there is retained moisture and the floor of a container is vented, the bacterial barrier properties of the filter assembly may be immediately compromised when exposed to a non-sterile atmosphere, while still at an elevated temperature (e.g., when the sterilization container is removed from the sterilization chamber).

This situation is of special concern when retained moisture is present and the containers are handled, stored or transported while they are still hot. Containers with vented bottoms are at particular risk of contamination due to the occurrence of undetected leaking of fluid around (or through) the vents when the contents are assumed to be sterile.

Consequently, rigid sterilization containers that do not form a fluid-proof seal, as well as a particulate seal, around the filtered vents are seriously limited and may be inappropriate for the multiple sterilization methods utilized by acute care facilities.

Seals currently used for filter vents for sterilization containers are unprotected and subject to damage, which can form fluid pathways which compromise their integrity, making the containers unsafe for multiple uses.

BRIEF DESCRIPTION OF THE INVENTION

The present invention provides a protected seal around the vent of a sterilization container that prevents particulate and fluid contaminants from entering the container after sterilization and even when moisture is retained in the container. The protection afforded the seal of the present invention permits multiple uses of a container without compromising the integrity of the sterilization process.

In the present invention, the filter and seal are protected. On the interior of the container, a gasket that forms a critical part of the seal is nested in a recess that surrounds the vent and is out of harm's way. On the outside of the container, a ridge surrounds the vent, protecting the sheet filter from damage.

Accordingly, it is an object of the present invention to provide a particulate and fluid seal for a sterilization container vent that is protected.

It is another object of the present invention to provide a seal having a gasket that is retained and protected in a recess.

It is a further object of the present invention to provide protection for both a sterilization container vent seal and a vent filter by a recess on the interior of the sterilization container which forms a ridge on the exterior of the container.

The foregoing and other objectives, features and advantages of the invention will be more readily understood upon consideration of the following detailed description of the invention taken in conjunction with the accompanying drawings.

BRIEF DESCRIPTION OF THE DRAWINGS

FIG. 1 is a top perspective view of a prior art rigid sterilization container having a lid with a vent formed by a pattern of small holes;

FIG. 2 is a perspective view of the underside of a lid of a rigid sterilization container (such as shown in FIG. 1) showing a vent surrounding a recess according to the invention;

FIG. 4 is a cross-sectional view FIG. 3;

FIG. 5 is the same as FIG. 4, except the parts are shown in their operative positions; and FIG. 6 is a top perspective view of a rigid sterilization container having a lid with a surrounding ridge according to the present invention.

DETAILED DESCRIPTION OF THE PREFERRED EMBODIMENTS

Figure 3:
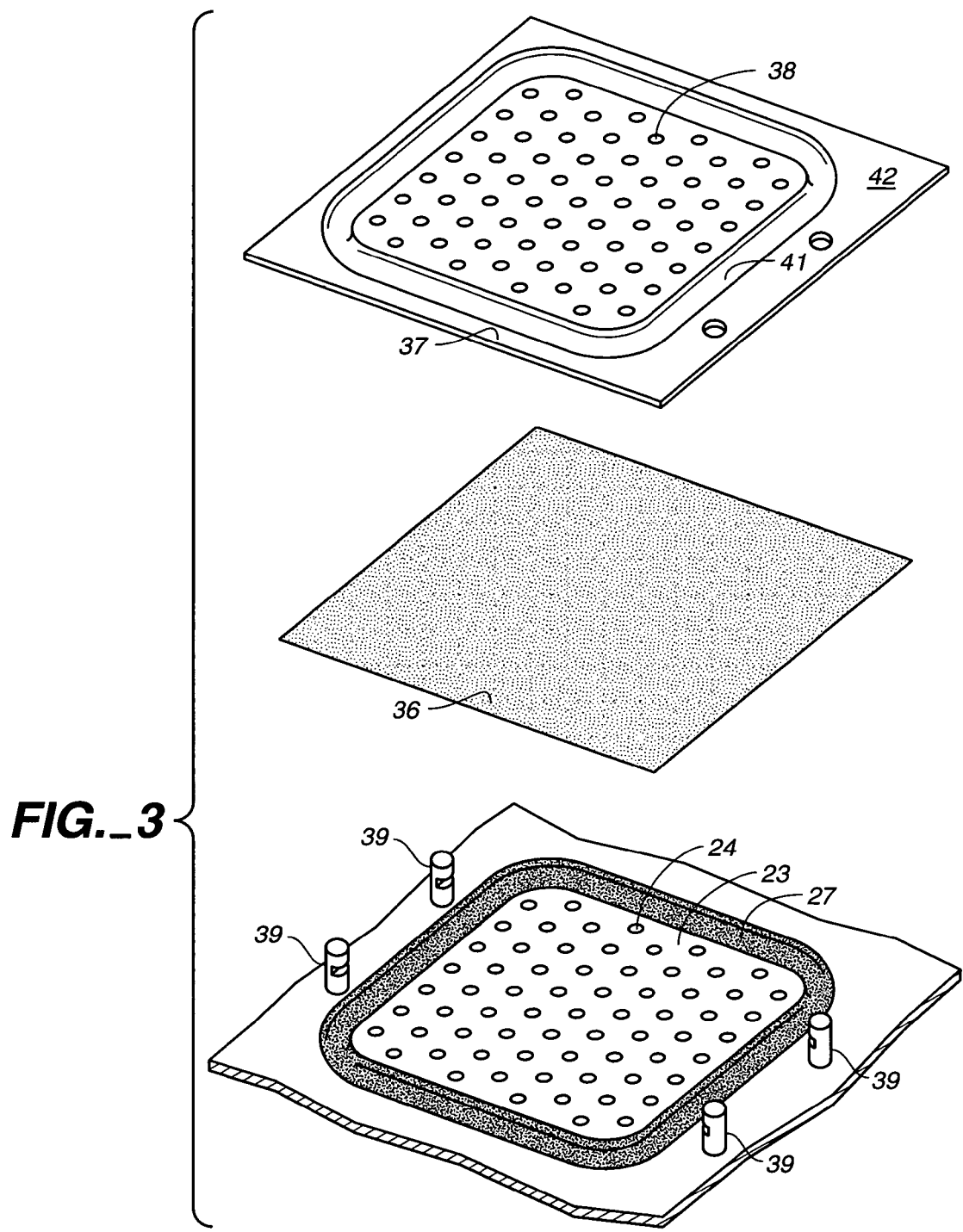
FIG. 3 an exploded view of a vent, sheet filter and filter cover of according to the invention with certain parts omitted.

It will be understood by those skilled in the art that the present invention can and should vary in dimension, depending, in part, on the shape and size of the ventilated area to be sealed.

Further, the present invention may be applicable to a number of materials, including, but not limited to, plastic, metal or any combination thereof so long as the material is resistant to conditions imposed by sterilization methods.

In addition, while the invention is described with reference to a vent in the lid of a container, it will be recognized by those skilled in the art that the invention is equally applicable to a vent in the bottom or side of a container and that vents of different geometric patterns than that illustrated are within the scope of the invention.

Referring to FIG. 1, a common design for a sterilization container 10 includes a vent 11 of a group of small holes 12 in the planar surface 13 of a lid 14. A sheet of filter material (not shown) typically covers the vent 11 on the interior of the lid 14 as a barrier against contamination. Because the holes 12 are in the same plane as the surface 13, it is not uncommon for something placed onto the external surface of the lid 14 at the location of the vent 11 to intrude into a hole 12, causing damage to the underlying filter.

Referring to FIGS. 2-5, according to the present invention, the interior surface 21 of a sterilization container lid 22 (vent planar member) has a vent 23 formed by holes 24 by which sterilization media can pass through vent planar member 22 into container 10. Although vent 23 is illustrated as a pattern of holes 24 forming a generally square shape, vent 23 could just as well be a plurality of holes forming a rectangular, circular or some other shape.

Surrounding the vent 23 on the interior surface 21 is a vent recess 26. A soft durometer gasket 27 constructed of temperature tolerant material (such as silicone) is bonded into the recess 26 and surrounds the vent 23. While the gasket 27 is shown having a generally arcuate rectangular cross-section and formed in a square circumferential shape, gasket 27 may have a different cross-section (round, oval, rectangular, triangular, etc.) to accommodate a different size and shape of the vent 23 and vent recess 26. Regardless of the geometry, the gasket 27 is in contact with substantially all of the surface of vent recess 26 and is wholly within the recess 26 so as not to extend above the planar surface 21 of lid 22.

The vent recess 26 can be formed by simply deforming the interior surface 21 so as to simultaneously form both the vent recess 26 below the surface 21 and the vent ridge 21 above the exterior surface 31.

A vent ridge 32 extends above (the lid is illustrated upside-down) the plane of the exterior surface 31 of lid 22 and surrounds the vent 23. In the preferred embodiment, the vent ridge 32 is the other side of the vent recess 26 (FIGS. 4 and 5). In other embodiments, the vent recess 26 and the vent ridge 32 can be separately formed. In either case, the recess and ridge work together to protect the vent from damage that could cause a breach of the seal.

A sheet filter 36 overlays the vent 23 at the interior surface 21 of lid 22 and is secured there by a generally planar filter cover 37 which has a pattern of cover holes 38 (cover vent) that are offset from vent holes 24 (FIG. 4) when cover 37 is mounted and locked in position by posts 39 and locking mechanism 40 (filter cover mounts and locking mechanism). Mechanisms for locking a filter cover to a vent using slots or aligning posts such as posts 39 and establishing positive pressure on the cover against the vent are well known in the art and therefore require no further description.

Filter cover 37 has a cover recess 41 that surrounds cover holes 38 on one of its sides 42 and a cover ridge 43 that surrounds cover holes 38 on its obverse side 44. The cover recess 41 and the cover ridge 43 can be formed as opposite sides of each other or separately.

As best seen in FIG. 5, when the vent cover 37 is locked in position over the vent 23 by a filter cover mounting and locking mechanism 39 and 40 with a sheet filter 36 therebetween (the sheet filter 36 is sized to extend over and cover the vent recess 36), the cover ridge 43 is forced against vent recess 26 with a positive pressure, causing filter 36 and gasket 27 to be compressed together between lid 23 and cover 37, establishing a fluid-tight seal surrounding the vent 23 and cover vent 38. The gasket 27 in the vent recess 26 is critical to the fluid-tight seal and must be undamaged to be an effective barrier against contamination.

Gaskets adhered to convex surfaces, as is the current practice, are exposed to damage. The vent recess 26 of the present invention provides a protected location for gasket 27, greatly reducing the possibility of damage that would compromise the seal formed around the vent 23 by the vent recess 26, gasket 27, sheet filter 36 and cover ridge 43 locking the elements together with a positive force.

While the recess 26 and ridge 43 may be approximately equal in size, the filter 36 and the gasket 27 between the two causes a space 46 to be established therebetween when the cover 37 is fully engaged. This space, which is greater than the thickness of filter 36, plays an essential role in the movement of sterilization media through the vent 23.

Typically, during a sterilization cycle, sterilizing media enters the interior of the container via the vent 23, through the sheet filter 36 which is disposed between the lid 22 and filter cover 37, while displaced atmosphere exits the same or another filtered vent. Any moisture formed in the sterilization container (not shown) is prevented from escaping the seal surrounding the vent and cover vent 38. Equally important, any fluid on the outside of the container near a vent is prevented from entering the container.

Referring to FIG. 6, the ridge 32 of lid 22 protects the filter 36 by preventing objects placed on top of the lid 22 from protruding into holes 24.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A particulate and fluid tight vent filter seal for a sterilization container having container planar members that enclose an interior space wherein one of the container planar members is a vent planar member that is a generally flat member that has an interior surface within the interior space, an opposing exterior surface and a container vent by which sterilization media can pass through the vent planar member into the interior space of the container, and a sheet filter disposed within the interior space of the container comprising:

a vent recess having a generally arcuate cross-section formed in the vent planar member by deformation of the vent planar member to create said arcuate vent recess on the interior surface of the vent planar member which recess extends below the plane of the interior surface and also creates a corresponding generally arcuate opposing protective ridge that extends above the plane of the exterior surface of the vent planar member wherein said recess and said ridge completely surround the container vent and wherein the sheet filter extends over the entire container vent and said surrounding vent recess;

a gasket having a generally arcuate cross-section secured wholly within said vent recess and in contact with substantially the entire concave surface of said vent recess whereby said gasket is protected against damage; and a generally planar filter cover that is disposed to move into engagement with the vent planer member and having a cover vent by which sterilization media can pass through said filter cover, said planar filter cover further comprising a generally arcuate convex cover ridge formed in said filter cover by deformation thereof wherein said cover ridge completely surrounds said cover vent and wherein said cover ridge is coextensive with said vent recess and sized to at least partially fit into said vent recess, whereby when said vent recess and said cover ridge are aligned and said filter cover is operatively secured in place, a positive force is applied to said cover ridge forcing it toward and in engagement with said gasket in said vent recess, whereby said cover ridge is forced against said sheet filter which, in turn, is forced against said gasket whereby said cover ridge, said gasket and said vent recess form a particulate and fluid tight seal that surrounds both the container vent and said cover vent which prevents fluid from entering or leaving the sterilization container through the seal so formed.

2. The vent filter seal of claim 1 wherein said cover vent and the container vent are spaced apart a distance greater than the thickness of the filter therebetween when said filter cover is operatively secured in place whereby lateral movement of sterilization media between the container vent and said cover vent is facilitated.

3. The vent filter seal of claim 2 wherein the container vent is a pattern of holes through the vent planar member and further wherein the vent in said filter cover is a pattern of holes through said filter cover within the area defined by said cover ridge wherein the holes of the container vent and said holes of the vent in said filter cover are offset relative to each other when said filter cover is operatively secured in place.

4. The vent filter seal of claim 1 wherein the vent planar member is in a removable container lid and said gasket is exposed when said filter cover is removed to change the filter.

* * * * *

UNITED STATES PATENT AND TRADEMARK OFFICE
CERTIFICATE OF CORRECTION

| | | |
|---|---|---|
| PATENT NO. | : 7,595,032 B2 | Page 1 of 1 |
| APPLICATION NO. | : 10/796643 | |
| DATED | : September 29, 2009 | |
| INVENTOR(S) | : Percival C. Banks | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 918 days.

Signed and Sealed this

Twenty-eighth Day of September, 2010

David J. Kappos
*Director of the United States Patent and Trademark Office*